(12) United States Patent
Zasloff et al.

(10) Patent No.: US 7,311,925 B2
(45) Date of Patent: Dec. 25, 2007

(54) METHODS AND COMPOSITIONS FOR BLOCKING MICROBIAL ADHERENCE TO EUKARYOTIC CELLS

(76) Inventors: Michael A Zasloff, 274 Linden La., Merion, PA (US) 19066; Glenn M Anderson, 8020 Fair View La., Norristown, PA (US) 19403

( * ) Notice: Subject to any disclaimer, the term of this patent is extended or adjusted under 35 U.S.C. 154(b) by 1033 days.

(21) Appl. No.: 10/053,299

(22) Filed: Jan. 17, 2002

(65) Prior Publication Data

US 2002/0131996 A1 Sep. 19, 2002

Related U.S. Application Data

(60) Provisional application No. 60/263,049, filed on Jan. 22, 2001.

(51) Int. Cl.
*A61K 9/48* (2006.01)
*A61K 9/20* (2006.01)
*A61K 9/14* (2006.01)

(52) U.S. Cl. .................. 424/451; 424/464; 424/489

(58) Field of Classification Search ............... 424/404, 424/464, 489
See application file for complete search history.

(56) References Cited

U.S. PATENT DOCUMENTS 6,388,056 B1 * 5/2002 Sundstrom et al.
6,607,711 B2 * 8/2003 Pedersen
6,770,306 B1 * 8/2004 Zeng

OTHER PUBLICATIONS

Webster's New Collegiate Dictionary 41 (1976).*
The Merck Index, An encyclopedia of Chemicals, Drugs, and Biologicals 883 (12th ed. 1996).*
Arvola T., Laiho K, Torkkeli S, Mykkanen H., Salminem S., Maumula L, and Isolauri E. Prophylactic Lactobacilius GG reduces antibiotic-associated diarrhea in children with respiratory infections:a randomized study. Pediatrics 104, e64, 1999.
Boris S and Barbes C. Role played by lactobacilli in controlling the population of vaginal pathogens. Microbes Infect. 2, 543-546, 2000.
Brighenti F, Casiraghi MC, Canzi E, and Ferrari A. Effect of consumption of a ready-to eat breakfast cereal containing inulin on the intestinal milieu and blood lipids in healthy male volunteers. European Journal of Clinical Nutrition 53, 726-733, 1999.
Du Toit M, Franz CM, Dicks, LM, Schillinger U., Haberer P, Warlies B., Ahrens F, and Holzapfel W.H. Characterization and selection of probiotic lactobacilli for a preliminary minipig feeding trial and their effect on serum cholesterol levels, faeces pH and faeces moisture content. Int. J. Food Microbiol. 40, 93-104, 1998.
Gionchetti P., Rizzello F., Venturi A., Brigidi P., Matteuzzi D, Bazzocchi , Poggioli G., Miglioli M., and Campieri M. Oral bacteriotherapy as a maintenance treatment in patients with chronic pouchitis: a double-blind, placebo-controlled trial. Gastroenterology 119, 305-309, 2000.

Guanalini S, Pensabebene L, Zikri MA, Dias JA, Casali LG, Hoekstra , Kolacek S, Massar K, Micetic-Turk D, Papadopoulou A, de Sousa JS, Sandhu B, Szajewska H, Weizman Z. Lactobacillus GG administered in oral rehydration solution to children with acute diarrhea: a multicenter European trial. J. Pediatr. Gastroenterol. Nutr. 30. 54-60, 2000.
Kelly CG and Younson JS. Anti-adhesive strategies in the prevention of infectious disease at mucosal surfaces. Expert Opin. Investig. Drugs 9, 1711-1721, 2000.
Martin H.L., Richardson, B.A., Nyange, P.M., Lavreys, L., Hillier S.L., Chohan B., Mandaliya K., Ndinya-Achola J.O., Bwayo J. and Kreiss J. Vaginal lactobacilli, microbial flora, and risk of human immunodeficiency virus type 1 and sexually transmitted disease acquisition. J. Infect. Dis. 180,1863-1868, 1999.
Merz AJ and So M. Interactions of pathogenic *Neisseriae* with epithelial cell membranes. Annu. Rev. Cell. Dev. Biol. 16, 423-457, 2000.
Mohan B., Kadirvel A., Natarajan A. and Bhaskaran M. Effect of probiotic supplementation on growth, nitrogen utilization and serum cholesterol in broilers. British Poultry Science 37, 395-401, 1996.
Mulvey MA, Schilling JD, Martinez JJ, Hultgren, SJ. From the cover: bad bugs and releagered bladders: interplay between uropathogenic *Escherichia col* and innate host defenses. Proc. Natl. Acad. Sci. USA 97, 8829-8835, 2000.
Nobaek S., Johansson M-L., Molin G., Ahrne S., and Jeppsson B. Alteration of intestinal microflora is associated with a reduction in abdominal bloating and pain in patients with irritable bowel syndrome. American Journal of Gastroenterology 1231-1238, 2000.
Petro T.M and Bhattacharjee J.K. Effect of dietary amino acid limitations upon native levels of murine immunoglobulins, transferrin, and complement. Infect. Immun. 27, 513-518, 1980.
Petro T.M and Bhattacharjee J.K. Effect of dietary amino acid limitations upon the susceptibility to *Salmonella typhimurium* and the effect upon humoral and cellular immune responses in mice. Infect. Immun. 32, 251-259, 1981.
Reid, G. Potential preventive strategies and therapies in urinary tract infection. World J. Urol. 17, 359-363, 1999.
Sobel, J. Bacterial Vaginosis. Annu. Rev. Med. 51, 349-356, 2000.
Vanderhoof JA, Whitney DB, Antonson DL, Hanner TL, Lupo JV, and Young, RJ. Lactobacillus GG in the prevention of antibiotic-associated diarrhea in children. Journal of Pediatrics 135: 564-568, 1999.
Venturi A., Gionchetti P., Rizzello F., Johansson R., Zucconi E., Brigidi P., Matteuzzi D., and Campieri M. Impact on the composition of the faecal flora by a new probiotic preparation: preliminary data on maintenance treatment of patients with ulcerative colitis. Aliment. Pharmacol. Ther. 13, 1103-1108, 1999.

* cited by examiner

*Primary Examiner*—Humera N Sheikh
(74) *Attorney, Agent, or Firm*—Henry E. Millson, Jr.

(57) ABSTRACT

A method of blocking microbial adherence to a eukaryotic cell surface in a mammal by applying a pharmacologically acceptable composition containing at least one compound selected from the group consisting of isoleucine, an active isomer thereof, and an active analog thereof, to said surface in a microbial blocking quantity. Also, compositions for achieving the above blocking of microbial adherence.

16 Claims, No Drawings

METHODS AND COMPOSITIONS FOR BLOCKING MICROBIAL ADHERENCE TO EUKARYOTIC CELLS

CROSS REFERENCE TO RELATED APPLICATIONS

This application claims the benefit of copending provisional application Ser. No. 60/263,049, filed on Jan. 22, 2001.

FIELD OF THE INVENTION

This invention relates to methods and compositions for preventing the adhesion of microorganisms to epithelial or other eukaryotic cell surfaces.

BACKGROUND OF THE INVENTION

Infection by microbial organisms involves initial adherence to a surface. Failure of adherence is believed to prevent subsequent invasion of otherwise intact epithelial surfaces. Hence methods have been developed/conceived to block infection through blockade of adherence. In general these approaches have focused on the development of substances which bind to either cellular receptors onto which bacteria dock, or substances which complex with microbial determinants, such as antibodies.

SUMMARY OF THE INVENTION

This invention relates to methods for blocking the adherence of microorganisms to epithelial cells and other eukaryotic cells by applying isoleucine to the surface of the cells, i.e. this invention relates to a method for preventing or treating microbial infections by the application or administration of a composition containing isoleucine.

The invention also relates to compositions containing at least one isoleucine compound for applying to the above cell surfaces.

DETAILED DESCRIPTION OF THE INVENTION

Other than in the operating examples, or where otherwise indicated, all numbers expressing quantities of ingredients or reaction conditions used herein are to be understood as modified in all instances by the term "about".

The method of the present invention is carried out by applying to a eukaryotic cell surface in a mammal a pharmacologically acceptable composition comprising at least one compound selected from the group consisting of isoleucine, an active isomer thereof, and an active analog thereof, to a eukaryotic cell surface in a microbial blocking quantity.

The microbial blocking quantity will vary depending on the isoleucine compound selected. In general, however, a quantity of from 0.1 ug/cm$^2$ to 1 gm/cm$^2$ of eukaryotic cell surface is effective, preferably from 3 ug/cm$^2$ to 100 ug/cm$^2$, and more preferably from 10 ug/cm$^2$ to 100 ug/cm$^2$.

Isoleucine stereoisomers that can be used in the present invention include L(+)-isoleucine, which is the naturally occurring form, DL-isoleucine, which is a racemic mixture and is the synthetic form, D(−)-allo-isoleucine, and L(+)-allo-isoleucine, although the latter two compounds are much less active. Active analogs of isoleucine include alpha-ketomethyl valerate, isoleucine hydroxamate, and isoleucine butyrate. When the term "isoleucine" is used hereinafter in the specification and claims, it is to be understood to include isoleucine, and active isomers and active analogs of isoleucine.

It should be noted that the quantity of L(+)-isoleucine in the typical mammalian diet is not sufficient to provide an effective microbial blocking quantity to eukaryotic cells.

The method of the invention will reduce microbial adherence on all eukaryotic cell surfaces exposed to microbes. These include the oral cavity, pharynx, respiratory tract, conjunctivae, gastrointestinal tract, skin, and the genitourinary tract, including the vagina, cervix, urethra and bladder. As such the present method can be used to prevent or treat infections or medical conditions caused by microbes whose attachment or growth on the surface of eukaryotic cells, including epithelial cells, can be comprised by an isoleucine induced state of "resistance" on the surface of the target cell.

Isoleucine is an essential amino acid, meaning that while it is critical for normal health and nutrition it cannot be synthesized within the body but must be obtained from an external source, usually via food intake. It is well established that a state of general malnutrition may lead to immune dysfunction and increased probability of infection. Specific withholding or nutritive limitation of any essential amino acid, including isoleucine, might likewise be expected to harm health or affect immune function. Such limitations do in fact affect certain immune parameters and resistance to certain experimental infections in mice (Petro T. M and Bhattacharjee J. K. Effect of dietary amino acid limitations upon native levels of murine immunoglobulins, transferrin, and complement. Infect. Immun. 27, 513-518,1980; and Petro T. M and Bhattacharjee J. K. Effect of dietary amino acid limitations upon the susceptibility to Salmonella typhimurium and the effect upon humoral and cellular immune responses in mice. Infect. Immun. 32, 251-259, 1981).

The approach taken in the implementation of the current invention does not relate to these general and specific states of starvation but rather confers health benefits upon hosts or patients in states of full nutrition as well as poor nutrition. The use of isoleucine as an adhesion inhibitor for the prevention and treatment of disease is further distinguished from its role as an essential nutrient in that may confer benefit after application to the surface of an epithelial layer (such as on the gums, in the vagina, in the nasal mucosa, on the skin, in the eyes, on wounds, in the GI tract, and the like), with no need for systemic digestive absorption, transport, processing, and utilization.

Because it can be expected that treatment with isoleucine will not affect the adhesion of all types or species of microbes equally, and because in humans and animals the microbes living on and near epithelial surfaces are in competition with one another for adhesion space and sites, treatment with isoleucine is expected to alter the numbers and relative abundance of various microbes that constitute the microbial flora of the epithelial surface and the anatomical compartment it surrounds. Such an effect of various other adhesion inhibitors has been observed and reported. See e.g. Kelly C G and Younson J S. Anti-adhesive strategies in the prevention of infectious disease at mucosal surfaces. Expert Opin. Investig. Drugs 9, 1711-1721, 2000. This probably accounts for the observation that the beneficial effects of the inhibitors often last substantially longer than the lifetime of the inhibitor in the treated compartment or surface. For example, bacteria such as lactobacilli compete with other bacteria in a host animal or human by a variety of mechanisms including competing for space, lowering the pH, and producing directly anti-microbial compounds to which they are themselves resistant (Boris S and Barbes C. Role played by lactobacilli in controlling the population of vaginal pathogens. Microbes Infect. 2, 543-546, 2000). Thus, an initial advantage given to lactobacilli by isoleucine may be maintained and propagated by other mechanisms. In this way altering the adhesion of microbes to an epithelial surface may dramatically change the relative numbers of various colonizing microbe species or types.

Hence, in addition to preventing or treating infection or other medical conditions by a direct effect of isoleucine on the adhesion of detrimental microbes to epithelial and other eukaryotic cells, isoleucine may have further beneficial effects by a resultant alteration of the populations of resident microflora. Examples of the benefits of promoting particular microflora are well documented and include the prevention and treatment of infectious diarrhea. See e.g. Arvola T., et al, Prophylactic *Lactobacillus* GG reduces antibiotic-associated diarrhea in children with respiratory infection: a randomized study, Pediatrics 104, 664, 1999; Vanderhoof J A, et al, *Lactobacillus* GG in the prevention of antibiotic-associated diarrhea in children. Journal of Pediatrics 135, 564-568, 1999; Guanalini S, et al, *Lactobacillus* GG administered in oral rehydration solution to children with acute diarrhea: a multicenter European trial. J. Pediatr. Gastroenterol. Nutr. 30, 54-60, 2000; the lowering of cholesterol and other blood lipids, see e.g. Mohan B., et al, Effect of probiotic supplementation on growth, nitrogen utilization and serum cholesterol in broilers. British Poultry Science 37, 395-401, 1996; Du Toit M, et al, Characterization and selection of probiotic lactobacilli for a preliminary minipig feeding trial and their effect on serum cholesterol levels, faeces pH and faeces moisture content. Int. J. Food Microbiol. 40, 93-104, 1998; Brighenti F, et al, Effect of consumption of a ready-to eat breakfast cereal containing inulin on the intestinal milieu and blood lipids in healthy male volunteers. European Journal of Clinical Nutrition 53, 726-733, 1999; resistance to sexually transmitted disease, see e.g. Martin H. L., et al, Vaginal *lactobacilli*, microbial flora, and risk of human immunodeficiency virus type 1 and sexually transmitted disease acquisition. J. Infect. Dis. 180, 1863-1868, 1999; resistance to urinary tract infections, see e.g. Reid, G. Potential preventive strategies and therapies in urinary tract infection. World J. Urol. 17, 359-363, 1999; resistance to bacterial vaginosis, see e.g. Sobel, J. Bacterial Vaginosis. Annu. Rev. Med. 51, 349-356, 2000; prevention of recurrence of inflammatory bowel disease, see e.g. Venturi A., et al, Impact on the composition of the faecal flora by a new probiotic preparation: preliminary data on maintenance treatment of patients with ulcerative colitis. Aliment. Pharmacol. Ther. 13, 1103-1108, 1999; Gionchetti P., et al, Oral bacteriotherapy as a maintenance treatment in patients with chronic pouchitis: a double-blind, placebo-controlled trial. Gastroenterology 119, 305-309, 2000; and relief from the symptoms of irritable bowel syndrome, see e.g. Nobaek S., et al, Alteration of intestinal microflora is associated with a reduction in abdominal bloating and pain in patients with irritable bowel syndrome. American Journal of Gastroenterology 1231-1238, 2000.

The method of the invention will either prevent adhesion of microbes to eukaryotic cells or will at least reduce their abundance.

The present method will work in man and other mammals, including companion animals and agricultural animals.

The invention also comprises a method of determining an effective dose of isoleucine comprising measuring the numbers and types of microbes contained in an epithelially lined compartment or contained in a sample taken from such a compartment, and adjusting the quantity of isoleucine accordingly. The methods of treatment described above pertain to, but are not limited to, the oral cavity and its surfaces, the entire respiratory tract and its surfaces, the entire gastrointestinal tract and its surfaces, the entire urogenitary tract and its surfaces, and the skin.

The invention also relates to pharmacologically acceptable compositions comprising:

A) from 0.001 to 99% by weight of isoleucine;

B) at least one additional pharmacologically active substance; and, optionally,

C) at least one pharmacologically acceptable carrier material.

In the above compositions, component A) is preferably present in from 0.002 to 50% by weight, and more preferably from 0.1 to 25% by weight.

Component B) substances will depend on the nature of the composition. For example, when the composition is a dental care product, component B) can be one or more of a fluoride, xylitol, an antibody, and an anti-microbial agent. The term "anti-microbial agent" is understood to include microbicides. When the composition is a nasal spray, component B) can be one or more of zinc ions, a decongestant, and an anesthetic. When the composition is in the form of a wound ointment or cream, component B) can be one or more of an antimicrobial substance or an anesthetic. When the composition is in the form of an oral supplement, component B) can be one or more of an antioxidant, a vitamin, probiotic bacteria, live bifidobacteria, live streptococci, live enterococci, heat-killed probiotic bacteria, peppermint oil or extract, menthol, quassia, bistort, ginger, angelica, bayberry, chamomile, fish oil, a fatty acid, an omega-3 fatty acid, fiber, flaxseed, slippery elm, niacin, a plant extract, garlic or garlic extract, calcium, stannol esters, lutein, zeaxanthin, cryptoxanthin, isoflavone, an anti-inflammatory compound, aspirin, ibuprofen, and acetaminophen. When the composition is in the form of a vaginal gel or douche, component B) can be one or more of an antifungal agent, an antibacterial agent, live probiotic microorganisms, and live lactobacilli. When the composition is an animal food component B) can be one or more of chicory, fiber, live probiotic bacteria, silage, grain, corn, soybeans, and wheat.

The invention also includes a composition comprising a rehydration solution containing glucose or other sugars and/or salts and isoleucine. The invention further includes a composition comprising an infant formula or food containing milk products and/or soy products and isoleucine. The invention also relates to gauze and other wound dressings containing or coated with isoleucine. The invention further relates to dental floss, ribbon, or tape coated with or impregnated with isoleucine. The invention also includes a composition comprising isoleucine and/or an active isomer thereof and methylcellulose or carageenan.

In addition, various other end use products can include isoleucine as the only pharmacologically active component.

Optional component C) can be one or more of a carrier material such as water, ethanol, oils, including those of petroleum, animal, vegetable or synthetic origin, such as peanut oil, soybean oil, mineral oil, sesame oil, and the like, an excipient such as methylcellulose, carageenan, and the like.

As discussed above, the invention encompasses various compositions containing isoleucine that are useful in the application of the subject methods. More specifically, the composition may be used to prevent the adherence of microbes to the surface of epithelial and other eukaryotic cells and to prevent or treat various disease states or conditions.

For example, the invention encompasses a method of treating or preventing diseases of the oral cavity by the administration of isoleucine containing compositions. The invention includes a method or a composition used to apply isoleucine to the epithelial surfaces of the oral cavity to prevent or treat, for example, gingivitis. The isoleucine containing composition may be applied as a dry powder, a paste, a gel, as a solution, in a chewing gum, in a lozenge, or via a device such as a dental floss or ribbon. The invention also relates to methods or compositions containing isoleucine useful in changing the numbers or relative numbers of microbes that reside in or on the surface of the oral cavity or gums. The present invention also encompasses compositions containing isoleucine and other substances that have utility in oral health but work by mechanisms distinct from that of isoleucine. Combining isoleucine with these substances is expected to result in a composition with greater activity than isoleucine or the individual ingredient when used as single agents due to additive or synergistic effects of the combined ingredients. Thus the invention specifically encompasses compositions containing isoleucine and fluoride, xylitol, an antibody, an anti-microbial substance, mint flavoring or extract, or a microbicidal substance.

The invention also relates to a method of preventing or treating various conditions or disease states of the urogenital tract. The invention includes a method or a composition used to apply isoleucine to the epithelial surfaces of the urogenital tract to prevent or treat, for example, bacterial vaginosis, urinary tract infection, or vaginal yeast infection. The isoleucine containing composition may be applied as a dry powder, a paste, as a solution, or in a gel. Specifically, a gel may be comprised of isoleucine in methylcellulose. The composition may also be used as a female douche. The invention also relates to methods or compositions containing isoleucine useful in changing the numbers or relative numbers of microbes that reside in or on the surface of the urogenital tract. Applications of isoleucine containing compositions may be used, for example, to increase the numbers or relative portion of *lactobacillus* species in the vagina to confer the known health benefits of increasing lactobacilli in that compartment. The present invention also encompasses compositions containing isoleucine and other substances that have utility in promoting urogenital health but work by mechanisms distinct from that of isoleucine. Thus the invention specifically encompasses compositions containing isoleucine and methylcellulose, carageenan, an antibody, a microbicidal substance, an anti-microbial substance, an anti-fungal antibiotic, or live probiotic bacteria such as lactobacilli.

The invention includes a method or a composition relating to a method of preventing or treating various conditions or disease states of the gastrointestinal tract. The invention also relates to methods or compositions used to apply isoleucine to the epithelial surfaces of the gastrointestinal tract to prevent or treat, for example, diarrhea, constipation, irritable bowel syndrome, or inflammatory bowel disease. The isoleucine containing composition may be ingested as a dry powder, a paste, as a solution, in a gel, as a tablet, lozenge, capsule, or bolus. The isoleucine containing composition may also be a food product such as yogurt, pudding, baked product, drink, soup, gum, candy, dairy product, infant formula, baby food, or rehydration solution. The invention specifically encompasses pre-measured dosage containers of an isoleucine containing composition such as a paper packet.

The invention also relates to use of isoleucine in changing the numbers or relative numbers of microbes that reside in or on the surface of the gastrointestinal tract. The present invention also encompasses compositions containing isoleucine and other substances that have utility in promoting gastrointestinal health but work by mechanisms distinct from that of isoleucine. Thus the invention specifically encompasses compositions containing isoleucine and peppermint oil or extract, menthol, quassia, bistort, ginger, angelica, bayberry, chamomile, slippery elm, a microbicidal substance, fiber, non-digestible carbohydrates, fructo-oligosaccharides, inulin, chicory, pre-biotic materials, flaxseed, live probiotic bacteria such as lactobacilli or bifidobacteria, fish oil, omega-3 fatty acids, fatty acids, or fractionated fish oil.

The invention also relates to a method of preventing or treating various conditions or disease states of the cardiovascular system by altering levels of cholesterol and certain other blood lipids. This beneficial alteration of lipid levels is a result of change in the numbers or relative numbers of gastrointestinal microbes that affect lipid metabolism. The invention includes a method or a composition used to apply isoleucine to the epithelial surfaces of the gastrointestinal tract to prevent or treat cardiovascular disease or increased blood lipid levels. The isoleucine containing composition may be ingested as a dry powder, a paste, as a solution, in a gel, as a tablet, capsule, or bolus. The isoleucine containing composition may also be a food product such as yogurt, pudding, spread, baked product, drink, soup, gum, candy, or dairy product. The present invention also encompasses compositions containing isoleucine and other substances that have utility in promoting cardiovascular health and/or the alteration of blood lipid levels but work by mechanisms distinct from that of isoleucine. Thus the invention specifically encompasses compositions containing isoleucine and one or more of a microbicidal substance, fiber, flaxseed, live probiotic bacteria such as lactobacilli or bifidobacteria, non-digestible carbohydrates, fructo-oligosaccharides, pre-biotic materials, fish oil, omega-3 fatty acids, fatty acids, fractionated fish oil, niacin, folic acid, garlic, calcium, stannol esters, luetin, zeaxanthin, cryptoxanthin, isoflavones, an anti-oxidant, vitamin C, vitamin E, an anti-inflammatory compound, aspirin, ibuprofen, acetaminophen, vitamin B12, vitamin B6, plant extracts, and other vitamins.

The invention also relates to a method of preventing or treating various conditions or disease states of the skin. The invention includes a method or a composition or device used to apply isoleucine to the epithelial surfaces of the skin to prevent or treat, for example, acne or fungal infection. The invention further includes a method or a composition or device used to apply isoleucine to treat a wound, prevent or treat wound infection, or to promote wound healing or closure. Thus the invention specifically encompasses a skin cream, ointment, gel, or solution containing isoleucine. Similarly the invention specifically encompasses a wound cream, ointment, gel, or solution containing isoleucine. The invention also includes a device such as a wound covering comprising cloth or gauze containing or impregnated with isoleucine. The invention also includes the use of isoleucine in changing the numbers or relative numbers of microbes that reside in or on the surface of the skin. The present invention also encompasses compositions containing isoleucine and other substances that have utility in promoting skin or wound health. Thus the invention specifically encompasses compositions containing isoleucine and one or more of a microbicidal substance, an anesthetic, and a cleaning agent.

The invention also relates to a method of preventing or treating various conditions or disease states of the respiratory tract. The invention includes a method or a composition used to apply isoleucine to the epithelial surfaces of the respiratory tract to prevent or treat, for example, the common cold, sinusitis, or lung infection. The isoleucine containing composition may be applied as a dry powder or particle, a paste, as a solution, as a spray, in a gum, in a lozenge, in a candy, or in a gel. The invention also relates to the use of isoleucine in changing the numbers or relative numbers of microbes that reside in or on the surface of the respiratory tract. The present invention also encompasses compositions containing isoleucine and other substances that have utility in promoting respiratory health but work by mechanisms distinct from that of isoleucine. Thus the invention specifically encompasses compositions containing isoleucine and one or more of a microbicidal substance, an anti-microbial substance, a decongestant, xylitol, diphenhydramine, pseudoephedrine, dextromethorphan, echinacea, and zinc ions.

The invention also relates to a method of preventing or treating various conditions or disease states of the ear. The invention includes a method or a composition used to apply isoleucine to the epithelial surfaces of the oral cavity, respiratory tract, or inner ear to prevent or treat, for example, otitis media. The isoleucine containing composition may be applied as a dry powder or particle, a paste, as a solution, as a spray, in a gum, in a lozenge, in a candy, in a syrup, or in a gel. The present invention also encompasses compositions containing isoleucine and other substances that have utility in promoting health of the ear and its associated structures but work by mechanisms distinct from that of isoleucine. Thus the invention specifically encompasses compositions containing isoleucine and one or more of a microbicidal substance, an antimicrobial substance, a decongestant, diphenhydramine, pseudoephedrine, xylitol, and zinc ions.

The invention also relates to a method of preventing or treating various conditions or disease states of companion animals. The invention includes a method or a composition used to apply isoleucine to the epithelial surfaces of the gastrointestinal tract, respiratory tract, oral cavity, gums, skin, or urogenital tract to prevent or treat, for example, diarrhea, constipation, halitosis, or gum disease. The isoleucine containing composition may be applied by any of the means described above including specifically as a toothpaste or food item. The present invention also encompasses compositions containing isoleucine and other substances that have utility in promoting the health of companion animals but work by mechanisms distinct from that of isoleucine. Thus the invention specifically encompasses compositions containing isoleucine and one or more of a microbicidal substance, non-digestible carbohydrates, fructo-oligosaccharides, chicory, live probiotic bacteria, and fiber.

The invention also relates to a method of preventing or treating various conditions or disease states and of promoting health and weight gain of agricultural or aqua-cultured animals. The invention includes a method or a composition used to apply isoleucine to the epithelial surfaces of the gastrointestinal tract, respiratory tract, oral cavity, gums, skin, or urogenital tract to prevent or treat, for example, diarrhea, respiratory infection, or the carriage of pathogenic organisms. The isoleucine containing composition may be applied by any of the means described above including specifically as spray or incorporated into the animals feed.

The present invention also encompasses compositions containing isoleucine and other substances that have utility in promoting the health of agricultural or aqua-cultured animals but work by mechanisms distinct from that of isoleucine. Thus the invention specifically encompasses compositions containing isoleucine and one or more of a microbicidal substance, chicory, silage, non-digestible carbohydrates, fructo-oligosaccharides, live probiotic bacteria, and grain.

The invention will be illustrated but not limited by the following examples.

EXAMPLES

Example 1

Treatment of Gingival Infection

In this example isoleucine was applied as a pure crystalline powder directly to the gums. The individuals were normal human volunteers. Each individual had clinically evident low grade gingivitis, as determined by the puffiness of the gingival margin and a history of some bleeding during normal dental brushing. Oral health care comprised twice daily flossing and dental brushing with a non-medicated toothpaste. No oral antiseptic was used. The individuals were not taking antibiotics. Isoleucine was applied by application of powder on the fingertip to the outer and inner gum margins of the upper and lower jaws. The entirety of the gingival surface was covered manually, twice daily. The AM application was performed following breakfast, immediately after brushing. The PM application was conducted prior to retiring for sleep.

Methods

Gingival surface was gently scrapped with the side of a rectangular glass cover slip and the material described was applied to a glass microscope slide and air-dried. The slide was stained in concentrated Giemsa stain for 1 min, then destained in water for 5 min. The slide was then air-dried and mounted with a cover slip cemented with Permount. Slides were examined by light microscopy at 100× and 400× magnification. Under these staining conditions bacteria were clearly visualized as dark blue particles against the pale gray epithelial cells.

Gingival scrapings were taken in the morning prior to normal oral care and prior to eating. Prior to scraping, the subject rinsed the mouth with a cup of water to wash free particulate matter, unattached cells, and bacteria.

Results

Scrapings were taken 3 days and 1 day prior to isoleucine administration and 1, 3, 5, and 7 days during isoleucine application. Gingival scrapings taken prior to isoleucine use revealed epithelial cells covered with numerous microcolonies. The bacteria adherent were represented by several different species, distinguished by morphology. Of 100 cells examined, greater than 90 exhibited adherent bacteria almost completely covering the surface of the epithelial cell. At least 200 bacteria were counted on the average on each cell.

A gingival smear taken on Day (−1) revealed numerous polymorphonuclear cells, a sign of inflammation. In addition, epithelial cells recovered were densely laden with adherent bacteria. Breath prior to oral hygiene in the AM, as evaluated by the examiner, was described as "bad". This odor is a byproduct of bacterial metabolism and resembles that of isobutyric acid.

Gingival smears taken on Day 1 following initiation of isoleucine application revealed little change in the number of epithelial cells covered with a dense coat of bacteria. Smears on Day 3 revealed dramatic reduction in adherent bacteria. Of 100 cells examined, now only 40 were fully covered with bacteria. No neutrophils were evident. Most cells had fewer than 100 total adherent bacteria. Most bacteria observed were isolated single or double forms. Few "microcolonies" representing contiguous groupings of greater than 4 organisms could be counted on these cells.

By Day 7, 5% of cells were fully covered with adherent bacteria, 15% had 1 to 10 bacteria/cell, and 80% were completely free of bacteria. Breath was described by an examiner, in the AM, prior to oral hygiene, as "free of odor."

Microbial Adherence to Gingival Epithelial Cells vs. Isoleucine Treatment (% cells)

| Day | 0 Bacteria | 1-10 Bacteria | 10-100 Bacteria | Contiguous lawn |
|-----|------------|---------------|-----------------|-----------------|
| −1  | 0          | 5             | 5               | 90              |
| 1   | 0          | 10            | 10              | 80              |
| 3   | 15         | 15            | 30              | 40              |
| 7   | 80         | 15            | 0               | 5               |

Example 2

Amelioration of Infectious Diarrhea

In this example isoleucine was administered to treat infectious diarrhea. In this example three individuals were naturally innoculated by a common agent. The nature of the diarrheal agent is not known. The duration of diarrhea was consistent with an infectious etiology. Isoleucine was utilized based on the hypothesis that reduction in microbial adherence would likely limit the continued re-infection of the gut wall by the agent, and/or prevent attachment of opportunistic commensal organisms.

Three members of a family traveling in the Middle East (MZ, BZ, JZ) contracted watery diarrhea, associated with food intolerance, following a meal they shared at a restaurant. Each individual had been in excellent health without prior history of GI complaints. All were unmedicated, including aspirin or antihistamines. Onset of gastrointestinal disturbance occurred in each individual within 5 hours and exhibited the same clinical characteristics. Diarrhea was watery, without gross blood, minimal mucous, slight fever with chills, no nausea, and persistence of hunger. Peristalsis was vigorous and increased by ingestion of food. Each individual was placed on a diet restricted to clear liquids (juices and soda), digestible carbohydrates (bread, rice, candy). No medications were administered.

Six days after ingestion of the diarrheal agent, one individual (MZ) was begun on oral isoleucine (ILE) therapy, while the other two continued on restricted diets. ILE (#E-2025 Bachem, lot 511191) was dissolved in distilled water to 0.001%. One glass of ILE solution (about 250 ml) was consumed every several hours. A total of about 4 liters was consumed over 3½ days. A reduction in stool frequency was noted within 12 hours of initiation of ILE therapy. This reduction continued gradually until the $3^{rd}$ day when no stools were passed. Food tolerance increased gradually over this period, with cheese and chicken tolerated by the $3_{rd}$ day. By day 4 following ILE treatment, a normal stool was passed and the diarrheal episode had passed.

BZ and JZ both continued to experience diarrhea unabated until about 11 days after ingestion of the infectious agent, with stool frequency decreasing noticeably. No stools were passed on day 12 and recovery was associated with return of food tolerance.

Thus, isoleucine therapy was associated with a shortening of the duration of diarrhea by approximately three days.

Example 3

Amelioration of Irritable Bowel Syndrome

In this example isoleucine was administered to individuals who experienced irritable bowel syndrome (IBS). IBS is a loosely defined condition associated with bowel discomfort including abdominal bloating, nausea, pain, and a sense of incomplete bowel movements. The etiology underlying IBS is unknown. It is our hypothesis that IBS results from adherence of certain "pathogenic" commensal organisms to the epithelial lining of certain segments of the GI tract, resulting in disturbance of normal host-bacteria relationships. Hence, reduction in the adherence of bacteria for the GI tract epithelium in this condition forms the basis of the use of isoleucine in IBS.

Two women, each in their mid-50's, presented with a history of IBS of over 20 years, in each case. In each, IBS was characterized by a sense of bloating experienced after eating cooked or raw vegetables, fruits, and meat. Each individual experienced urgency to move her bowels several times a day to an extent that often awakened the individuals from sleep. Bloating was accompanied by abdominal discomfort, described as mild cramps. Individuals felt "gassy" most of the day. Each individual was given isoleucine, 1 tsp, twice a day, each dose mixed in ½cup of yogurt. The yogurt was included to promote reinoculation of the GI tract with probiotic "good" bacteria. In each case, it was known from previous experience that yogurt itself had little effect on the IBS experienced by these individuals. Within 2 days of isoleucine administration, bloating, urgency to defecate, and gassiness had disappeared. Both individuals described the state of their bowel function as "normal", for the first time in 20 years. Each individual was maintained on isoleucine for 1 month with consistent response. Each was then withdrawn from isoleucine, and provided yogurt unsupplemented with isoleucine. Within about 2 days both women recorded a reappearance of the former symptoms of IBS.

Example 4

Amelioration of Bacterial Vaginosis

In this example isoleucine was administered locally to the vagina to treat the symptoms of bacterial vaginosis. By inhibiting the adherence of bacteria to the wall of the vagina, microbial growth, inflammation, and associated signs of malodorous discharge and symptoms such as pruritis can be treated.

A 26 year old white female, with a normal menstrual cycle and in excellent health, experienced vaginal irritation and malodorous discharge associated with her cycle, generally beginning several days prior to the onset of her period. Isoleucine was self-administered as a powder locally within the vaginal cavity digitally, twice a day. Within 2 days symptoms of vaginosis disappeared. Isoleucine therapy was continued for several days following termination of menstrual discharge, and then stopped. The individual remained symptom free following cessation of isoleucine administration. Isoleucine was again administered during the following months, cycled as described initially. Based on the symptoms and signs, the chronic vaginosis appears to have been effectively cured.

What is claimed is:

1. A method of blocking microbial adherence to a eukaryotic cell surface in a mammal by applying to said surface a pharmacologically acceptable composition consisting essentially of an amino acid component selected from the group consisting of at least one of the following L(+)-isoleucine, DL-isoleucine, D(−)-allo-isoleucine, L(+)-allo-isoleucine, and active analogs of isoleucine present in a microbial blocking quantity, wherein the microbial blocking quantity is in the range of from about 0.1 ug/cm$^2$ to about 1gm/cm$^2$ of eukaryotic cell surface area.

2. The method of claim 1 wherein said quantity is from about 3 ug/cm$^2$ to about 100 ug/cm$^2$.

3. The method of claim 1 wherein said quantity is from about 10 ug/cm$^2$ to about 100 ug/cm$^2$.

4. The method of claim 1 wherein the mammal is mankind.

5. The method of claim 1 wherein the epithelial surface is one or more of the pharynx, GI tract, urinary tract skin, and eye.

6. The method of claim 1 wherein the composition consists of a pure powder of L(+)-isoleucine and/or DL-isoleucine.

7. The method of claim 1 wherein the composition is in the form of a dry powder, a paste, a solution, a gel, a tablet, a lozenge, or a capsule.

8. The method of claim 1 wherein the composition is directly applied to the said epithelial surface.

9. The method of claim 1 wherein the method is used to treat an infection caused by microbes.

10. The method of claim 9 wherein the microbes are bacteria.

11. The method of claim 1 wherein the amino acid component is selected from at least one of the following: L(+)-isoleucine, DL-isoleucine, D(−)-allo-isoleucine, and L(+)-allo-isoleucine.

12. The method of claim 1 wherein the composition is in the form of a skin ointment or cream.

13. The method of claim 1 wherein the composition is in the form of a dental care product.

14. The method of claim 1 wherein the composition is in the form of a wound ointment or cream.

15. The method of claim 1 wherein said composition also contains at least one additional pharmacologically active substance selected from the group consisting of a fluoride, xylitol, an antibody, an anti-microbial agent, zinc ions, a decongestant, an anesthetic, an anti-oxidant, a vitamin, a microbial substance, a pre-biotic material, folic acid, echimacea, peppermint oil or extract, menthol, quassia, bistort, ginger, angelica, bayberry, chamomile, fish oil, or fractionated fish oil, a fatty acid, fiber, flaxseed, a plant extract, garlic or garlic extract, calcium, stannol esters, lutein, zeaxanthin, cryptoxanthin, isolfiavone, an anxi-inflammatory compound, an antifungal agent, and a food product; and optionally, Pharmacologically acceptable carrier materials and/or excipients.

16. The method of claim 1 wherein the composition also contains an antifungal and/or antimicrobial substance.

* * * * *